US005506129A

United States Patent [19]

Sangar

[11] Patent Number: 5,506,129

[45] Date of Patent: Apr. 9, 1996

[54] VIRUS PRODUCTION

[75] Inventor: David V. Sangar, Beckenham, United Kingdom

[73] Assignee: Evans Medical Limited, England

[21] Appl. No.: 348,156

[22] Filed: Nov. 28, 1994

Related U.S. Application Data

[63] Continuation of Ser. No. 142,400, Dec. 1, 1993.

[30] Foreign Application Priority Data

May 24, 1991 [GB] United Kingdom .................... 9111230

[51] Int. Cl.[6] ............................... C12N 7/00; C12N 7/01; C12N 7/04; C12N 7/08

[52] U.S. Cl. ........................ 435/239; 435/235.1; 435/236; 435/240.1; 435/237; 424/184.1; 424/226.1

[58] Field of Search ............................. 424/184.1, 226.1; 435/235.1, 236, 240.1, 239, 237

[56] References Cited

U.S. PATENT DOCUMENTS

| | | | |
|---|---|---|---|
| 4,123,520 | 10/1978 | Hagopian et al. | 424/92 |
| 4,164,566 | 8/1979 | Provost et al. | 424/89 |
| 4,301,249 | 3/1981 | Markus et al. . | |
| 4,460,575 | 7/1984 | d'Hinterland et al. | 424/92 |
| 4,721,675 | 1/1988 | Chan et al. | 435/239 |
| 4,724,206 | 2/1988 | Rupp et al. | 435/68 |
| 4,753,796 | 6/1988 | Moreno et al. | 424/92 |
| 4,755,381 | 7/1988 | Cryz et al. | 424/92 |
| 4,783,407 | 9/1988 | Provost et al. . | |
| 4,877,613 | 10/1989 | Vedros et al. | 424/92 |
| 5,021,348 | 6/1991 | Giesa et al. | 435/237 |
| 5,182,109 | 1/1993 | Tamura et al. | 424/92 |

FOREIGN PATENT DOCUMENTS

| | | |
|---|---|---|
| 0025745 | 4/1981 | European Pat. Off. . |
| 0302692 | 8/1989 | European Pat. Off. . |

OTHER PUBLICATIONS

Flehmig 1981 Hepatitis A Virus in Cell Culture. Med. Microbiol. Immunol. 170:73–81.

Kojima et al. 1981. Propagation of Human Hepatitis A Virus in Conventional Cell Lines. J. Medical Virol. 7:273–286.

Gauss–Müller et al. 1981. Propagation of Hepatitis A Virus in Human Embryo Fibroblasts. J. Med. Virol. 7:233–39.

Binn et al. 19 "Primary Isolation and Serial Passage . . . " J. Clinical Microbiol 20(1):28–33.

Westphal et al., 1965, Bacterial lipopolysaccharide extraction with phenol–water and further application of the procedure. Methods Carbohydrate Chemistry, 5:83–91.

Stepanenko et al., 1972, Precipitation of neutral polysaccharides and separation of their mixtures by use of various quarternary salts, Carbohydrate Research, 25:526–530.

Molecular Biology of The Cell, Second Edition Ablerts et al p. 307 Membrane Transport of Small Molecules.

Gust et al, J. Infectious Diseases 151, No. 2, 365–367 "The Origin of the HM 175 Strain of Hepatitis A Virus".

Binn et al, J. Clinical Microbiology 20, No. 1, 28–33 "Primary Isolation and Serial Passage of Hepatitis A Virus Strains in Primate Cell Cultures".

Borovec et al J. Virology, 67, No. 6, 3095–3102 "Synthesis and Assembly of Hepatitis A Virus–Specific Proteins in BS–C–1 Cells".

Vaccine, vol. 8, 1990, pp. 513–514; Kusov, "Characteristics of Inactivated Hepatitis A Vaccine".

Journal of Medical Virology 24, 1988, pp. 369–376, Widell et al Enhancement of Hepatitis A Propagation.

*Primary Examiner*—James C. Housel
*Assistant Examiner*—N. M. Minnifield
*Attorney, Agent, or Firm*—Nixon & Vanderhye

[57] ABSTRACT

A process for the propagation of hepatitis A virus, which process comprises culturing cells infected with the virus in an aqueous culture medium in which the concentration of sodium chloride is from 30 mM to 170 mM above the isotonic concentration of sodium chloride; and production of a vaccine therefrom.

16 Claims, 1 Drawing Sheet

VIRUS PRODUCTION

This is a Rule 60 continuation of of application Ser. No. 08/142,400, filed Dec. 1, 1993.

The invention relates to an improved process for increasing the yield of Hepatitis A virus grown in a culture medium.

BACKGROUND OF THE INVENTION

Hepatitis A virus (HAV) is a member of the Picornaviridae (Melnick, J. L. (1982), Intervirology, 18, 105–106). It is endemic throughout the world and can cause large outbreaks of disease (W.H.O. 1988, Weekly Epidemiological Record, 65, 91–92). Protection is afforded by administration of immune human IgG as at present there is no vaccine available. Killed virus vaccines are now under clinical trials but the production of a cost-effective vaccine is hampered by the low yields of virus obtained from tissue culture systems. Attempts have been made to improve the virus yield and it has been reported that the cellular RNA polymerase-2 inhibitor 5,6-dichloro1-β-d-ribofuranosylbenzimidazole increases yields by 200–300% when incorporated into the culture medium.

A demonstration that HAY would grow in tissue culture (Provost, P. J. & Hillerman, M. R. (1979), Proceeding Society Experimental Biology and Medicine, 160, 213–221) was a considerable advance for the study of the virus. Since that time strains of hepatitis A have been developed that grow more rapidly and to a higher titre than the original isolates. However, compared to other picornaviruses, the yields are still low and the time to obtain maximum yield is long. There are reports that the use of host enzyme inhibitors can increase the yield of HAV (Widdell, A., Hansson, B. G., Nordenfelt, E. and Oberg, B. (1988), Journal of Medical Virology, 24, 369–376), however these are expensive and are unlikely to be cost effective for virus production for the preparation of vaccines.

SUMMARY

According to the present invention, there is provided a process for the propagation of hepatitis A virus, which process comprises culturing cells infected with the virus in an aqueous culture medium in which the concentration of sodium chloride is from 30 mM to 170 mM above the isotonic concentration of sodium chloride. Thus, an improved process is provided for increasing the yield of HAV which is simple and inexpensive.

DESCRIPTION OF THE PREFERRED EMBODIMENTS

Figure 1:
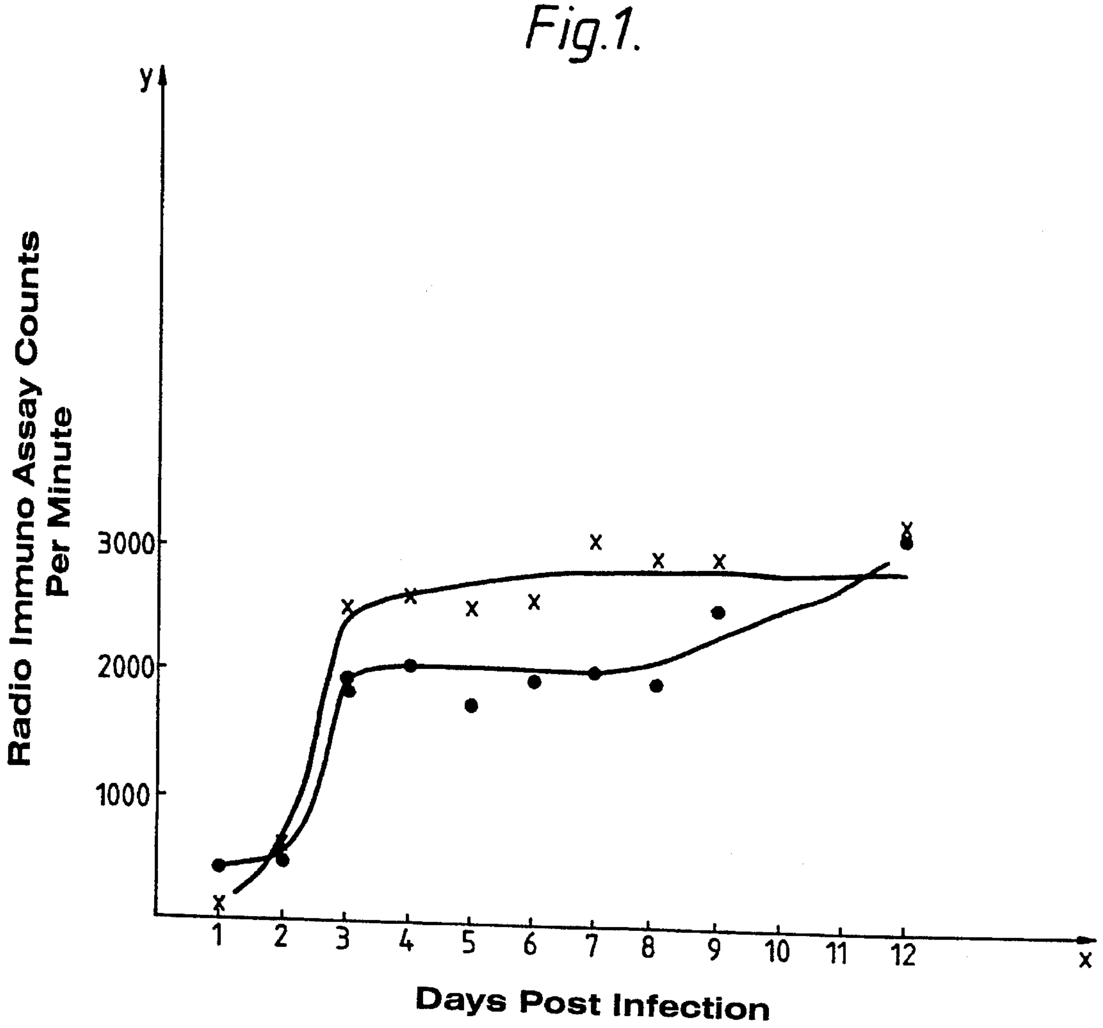
FIG. 1 illustrates the rate of production of HAV in media containing and media not containing excess sodium chloride.

The concentration of sodium chloride in the medium may be from 50mM to 150mM greater than the culture's isotonic concentration of sodium chloride. A preferred concentration is from 80mM to 120mM, most preferably 100mM, above the isotonic concentration of sodium chloride for the culture. Typically, the isotonic concentration of sodium chloride is approximately 150mM for media in which cells infected with hepatitis A virus are grown.

If the isotonic concentration of sodium chloride for a culture is known, the absolute concentration of sodium chloride in the culture medium may be deduced. Hepatitis A virus may therefore be grown by the present process in an aqueous culture medium in which the absolute concentration of sodium chloride is from 180mM to 320mM. Suitable absolute concentrations of sodium chloride in a culture medium are from 200mM to 300mM, preferably from 230mM to 270mM. A particularly useful absolute concentration of sodium chloride in a culture medium is about 250mM.

The concentration of sodium chloride in the culture medium may be raised above the isotonic concentration by adding aqueous sodium chloride the culture medium. The additional sodium chloride may be added to the culture before, simultaneously with or after infection of cells in culture with hepatitis A virus. Any appropriate strain of hepatitis A virus may be employed. Advantageously, an aqueous solution of sodium chloride is added to the culture medium from 12 to 48 hours, suitably about 24 hours, after infection of the cells in the culture with the virus.

Cells which are suitable for use in the present process are typically cells of cell lines which will support the growth of hepatitis A virus and, in particular, of cell lines which are acceptable for the production of vaccines. However, any type of cell culture system in which the virus is capable of replicating may be employed. The cell culture system may therefore be formed of primary, continously cultivated or transformed cells. The cell system may be derived from kidney or liver of human or nonhuman primate origin.

Examples of suitable cell culture systems include those derived from fetal or new born kidney cells from rhesus monkey, cynomolgus monkey, marmoset or cercopithecus monkey, or diploid fibroblast cells derived from human or non-human primate lung tissue such as, for example, WI-38 or MRC-5 cell lines (US-A-4301249); Vero cells (US-A-4783407); human liver tumor lines PLC/PRF/5 or Hep. G2 (US-A-4721675); or BS-C-1 cells.

A suitable strain of hepatitis A virus is the HM 175 strain, in particular its 18F isolate. "The origin of the HM 175 strain of hepatitis A virus" was described by Gust, Lehmann, Crowe, McCrorie, Locarnini and Lucas (Journal of Infectious Diseases, Vol. 151, No. 2, 365–67). The adaptation of this virus to grow in tissue cultures is described in "Primary isolation and serial passage of hepatitis A virus strains in primate cell cultures" by Binn, Lemon, Marchwicki, Redfield, Gates and Bancroft (Journal of Clinical Microbiology, Vol. 20, No. 1, 28–33).

The process may take place in any type of cell culture medium in which the cells infected with the virus are capable of growing. The medium may further comprise nutrients required for the growth of the cells, generally a source of assimilable carbon, a source of assimilable nitrogen and, optionally, mineral salts. An example of a particularly suitable cell culture medium is Eagles Minimum Essential Medium supplemented with foetal calf serum.

The cells may be infected with the virus by any conventional method. The conditions under which the infected cell lines are propagated depend upon the nature of the cell line used. Advantageously, the infected cells are incubated at the temperature which is known to produce maximum growth rate. A cell culture may be incubated at 25° C. to 40° C., for example from 34° C. to 37° C. Cell growth may be sustained until the cytopathic effect is complete. Culture of the cells infected with the virus in the aqueous culture medium containing additional sodium chloride may be grown for 2 to 4 days.

The virus obtained by the process of the present invention may be isolated, purified, and inactivated. Inactivated Hepatitis A thus prepared may be formulated with a pharmaceutically acceptable carrier or diluent in order to produce a vaccine therefrom. Accordingly, the invention also provides a vaccine comprising a pharmaceutically acceptable carrier or diluent, and as an active ingredient, inactivated hepatitis A virus produced by the present process.

The following Example illustrates the invention. In the accompanying drawing, the Figure illustrates the rate of production of HAV in media containing (x—x) and media not containing (●—●) excess sodium chloride. The x-axis denotes days post infection. The y-axis denotes radioimmunoassay counts per minute.

EXAMPLE

Cell Culture

BS-C-1 cells were obtained from the American Type Culture Collection (ATCC CCL 26) and used between passages 53 and 75 (Hopps et al. (1963), Journal of Immunology, 91 416–424 and Lemon et al. (1983), Journal of Clinical Microbiology, 17 834–839). The cells were grown in 1969 medium (Seefried, A., Healy, G. M., and Macmorine, H. G., (1970), Jugoslavenka Akademija Znanosti I Umjetnosti (Symposium on human diploid cells) and Healy, G. M., Teleki, S., Seefried, A., Walton, M. J., and Macmorine, H. G., Applied Microbiology, (1971), Vol. 21, No. 1, 1–5) containing 10% foetal calf serum (FCS).

Virus Growth

Confluent BS-C-1 cell monolayers were infected with virus harvest to give approximately 1 to 10 radioimmunofocus units/cell (Lemon et al., (1983) Journal of Clinical Microbiology, 17, 834–839) of HAV per cell for 1 hr at room temperature. The virus used was the 18F tissue culture adapted isolate of the HM175 variant of HAV provided by Dr. S. Lemon. The sheets were washed in Eagles Minimum Essential Medium (MEM) and incubated at 34° C. in Eagles MEM containing 2% FCS. Different concentrations of sodium chloride (NaCl) were added, usually 24hr later. At various time intervals after infection the flasks were placed at −20° C.

Preparation Of Virus Antigens

The cells were subjected to three cycles of freeze-thawing. Cell debris was pelleted by low speed centrifugation and resuspended in 10 mM TRIS, 10mM NaCl, 1.5 mM $MgCl_2$, 1% Nonidet P40 and 0.5% alkyl dimethylamine betaine (Empigen, Albright and Wilson Chemicals). The suspension was incubated for 1 hr at room temperature. The resulting suspension was clarified by low speed centrifugation and the supernatant was added to the supernatant obtained from the freeze-thawed cells. This was used for radioimmunoassay (RIA) or radioimmunofocus assay (RIFA) directly.

Alternatively, the virus solution was made with 100 mM TRIS pH 7.6, 100 mM NaCl, 3mM EDTA and sarkosyl added to 1%. After 1 hour at 37° C. the virus was pelleted by centrifugation at 100,000 x g at 5° C. for 18 hrs. The virus pellet was resuspended in 200ml 100mM TRIS pH 7.6 and 100mM NaCl and used for RIA or RIFA.

Radioimmunoassay (RIA)

RIA was done as described by Lemon, et al., (1982), J. Medical Virology, 10, 25–36. Briefly, virus was captured using an anti-HAV polyclonal antiserum. After washing, the captured antigen was detected using polyclonal anti-HAV $^{125}$I IgG.

Radioimmunofocus assay (RIFA)

HAV infectivity was determined by RIFA (Lemon et al., (1983), J. Clinical Microbiology, 17, 834–839). Virus was absorbed for 1h at room temperature and the cells then overlayed in Eagles MEM supplemented with 2% FCS and containing 0.5% agarose. Cells were incubated under 5% $CO_2$ for 7 days at 35° C. After acetone fixation of the cell sheet, foci of virus replication were detected by reaction with $^{125}$I anti-HAY polyclonal IgG followed by autoradiography.

RESULTS

The addition of 100 mM NaCl to growth medium consistently gave a more rapid cytopathic effect (CPE). Usually by 7 days post-infection CPE was complete although this was not observed in control cultures even at 10 days post-infection. Table 1 shows the yield of HAV, as measured by radioimmunoassay. There was an apparent increase in yield both in the initial harvest and in the material concentrated by ultracentrifugation.

TABLE 1

| | Harvest | | Concentrated by ultracentrifugation | |
|---|---|---|---|---|
| Dil* | Control | +100 mM NaCl | Control | +100 mM NaCl |
| 1/1 | 153 | 379 | 744 | 1788 |
| 1/10 | 204 | 252 | 264 | 359 |
| 1/100 | 120 | 142 | 179 | 179 |

*the dilution 1/1 in Table 1 is the combination of virus in cell supernatant plus that removed from the cells by detergent. The material used to infect the cell monolayer was the virus in the supernatant only, and would be about 50% of the total virus. Dilutions 1/10 and 1/100 are 10-fold and 100-fold dilutions of the 1/1 dilution respectively.

To determine the optimum concentration of sodium chloride for enhancing the virus yield, cells were infected with virus and after 24hrs various concentrations of sodium chloride were added. Cells were harvested 7 days later and the virus yield determined by RIA and by RIFA. The results are given in Table 2.

TABLE 2

| Extra NaCl (mM) | RIA cpm (−Bg) | RIFA |
|---|---|---|
| 0 | 64 | $5 \times 10^5$/ml |
| 50 | 113 | $8 \times 10^5$/ml |
| 100 | 169 | $1.2 \times 10^6$/ml |
| 150 | 134 | $7 \times 10^5$/ml |
| 200 | 30 | $1 \times 10^5$/ml |
| 250 | 11 | $3 \times 10^3$/ml |

Growth Curve of HAY with or without Extra Salt

Since one effect of hypertonic NaCl was to increase the rate of the CPE and because the previous experiments had been terminated at 7 days post-infection, it was considered important to determine whether elevated levels of NaCl increased the absolute yield or simply increased the rate at which HAY was produced. 25 cm flasks were infected with 10 radioimmunofocus units per cell and incubated with or without extra sodium chloride (100 mM), which was added immediately post-infection. Flasks were harvested at 24 h intervals and the virus extracted and concentrated by ultracentrifugation. Elevated concentrations of NaCl appeared to make little difference to the rate of virus production (FIG. 1). The greatest increase was between day 2 and day 3 in both cases, maximum yield being obtained between day 3 and 4. Although there was an increase in yield with additional NaCl, this enhancement was considerably lower than in previous experiments. This may be related to the fact that in earlier experiments the extra NaCl was added 24 hr post-infection whereas in this experiment it was added immediately after infection.

I claim:

1. A process for the propagation of hepatitis A virus, which process comprises culturing cells infected with the virus in an aqueous culture medium in which the concentration of sodium chloride is from 80 mM to 170 mM above the isotontc concentration of sodium chloride.

2. A process according to claim 1, wherein the concentration of sodium chloride is from 80mM to 120mM above the isotonic concentration of sodium chloride.

3. A process according to claim 2, wherein the concentration of sodium chloride is about 100mM above the isotonic concentration of sodium chloride.

4. A process according to claim 1, wherein an aqueous solution of sodium chloride is added to the culture medium from 12 to 48 hours after infection of the cells in the culture with the virus.

5. A process according to claim 1, wherein the cell culture comprises BS-C-1 cells.

6. A process according to claim 1, wherein the culture medium comprises Eagles Minimum Essential Medium and foetal calf serum.

7. A process according to claim 1, wherein the said culturing is effected for from 2 to 4 days.

8. A process according to claim 1, which further comprises recovering the hepatitis A virus thus grown.

9. A process according to claim S, which further comprises inactivating the recovered hepatitis A virus.

10. A process for the preparation of a vaccine against hepatitis A virus which process comprises culturing cells infected with the virus in an aqueous culture medium in which the concentration of sodium chloride is from 30mM to 170 mM above the isotonic concentration of sodium chloride, recovering the hepatitis A virus thus grown, inactiveting the recovered hepatitis A virus and formulating the inactivetad hepatitis a virus with a pharaceutically acceptable carrier or diluent.

11. A process according to claim 10, wherein the concentration of sodium chloride is from 80 mM to 120 mM above the isogonic concentration of sodium chloride.

12. A process according to claim 11, wherein the concentration of sodium chloride is about ϕmM above the isogonic concentration of sodium chloride.

13. A process according to claim 10, wherein an aqueous solution of sodium chloride is added to the culture medium from 12 to 48 hours after infection of the cells in the culture with the virus.

14. A process according to claim 10, wherein the cell culture comprises Be-C-1 cells.

15. A process according to claim 10, wherein the culture medium comprises Eagles Minimum Essential Medium and foetel calf serum.

16. A process according to claim 10, wherein the said culturing is effected for from 2 to 4 days.

* * * * *